United States Patent [19]
Hamprecht et al.

[11] 3,992,444
[45] Nov. 16, 1976

[54] PRODUCTION OF SULFAMIC ACID HALIDES

[75] Inventors: Gerhard Hamprecht, Mannheim; Dietrich Mangold, Neckargemuend; Karl-Heinz Koenig, Frankenthal, all of Germany

[73] Assignee: BASF Aktiengesellschaft, Ludwigshafen (Rhine), Germany

[22] Filed: Sept. 16, 1974

[21] Appl. No.: 506,604

[30] Foreign Application Priority Data
Dec. 23, 1971 Germany .............................. 2164176

Related U.S. Application Data

[63] Continuation-in-part of Ser. No. 316,534, Dec. 19, 1972, abandoned.

[52] U.S. Cl. ............................................ 260/543 R
[51] Int. Cl.² ...................................... C07C 143/72
[58] Field of Search ...................... 260/543 R, 513.6

[56] References Cited
UNITED STATES PATENTS

| | | | |
|---|---|---|---|
| 2,785,196 | 3/1957 | Bieber | 260/513.6 |
| 2,800,501 | 7/1957 | Thompson | 260/513.6 |
| 3,673,247 | 6/1972 | Hill | 260/543 R |
| 3,673,259 | 6/1972 | Rosin | 260/543 R |
| 3,706,794 | 12/1972 | Horner | 260/543 R |

FOREIGN PATENTS OR APPLICATIONS

| | | | |
|---|---|---|---|
| 793,231 | 6/1973 | Belgium | 260/547 R |
| 1,943,233 | 3/1971 | Germany | 260/543 R |

OTHER PUBLICATIONS

Hansen, Acta. Chem. Scand., 17 (1963) No. 7, pp. 2141–2142.

*Primary Examiner*—Anton H. Sutto
*Attorney, Agent, or Firm*—Johnston, Keil, Thompson & Shurtleff

[57] ABSTRACT

The production of sulfamic acid halides by reaction of sulfamic acids with acid halides, and the new sulfamic acid halides. The products are starting materials for the production of plant protection agents, dyes and pharmaceuticals.

10 Claims, No Drawings

PRODUCTION OF SULFAMIC ACID HALIDES

This application is a continuation-in-part of U.S. application Ser. No. 316,534, filed on Dec. 19, 1972, now abandoned.

The present invention relates to sulfamic acid halides and a process for the production of sulfamic acid halides by reaction of sulfamic acids with acid halides.

Whereas alkyl- or arylsulfonyl chlorides (alk-SO$_2$Cl, ar-SO$_2$Cl) constitute a class of substances known for more than 100 years, N-alkylaminosulfonyl chlorides (alk-NHSO$_2$Cl) are a class of compounds which have hitherto been investigated only to a very small extent and which are extremely difficultly acessible. On account of the possible elimination of hydrogen chloride to unstable sulfenes (RN=SO$_2$) doubt was cast on the existence of these compounds in the art until very recently (L. Audrieth, A. Vandi and Th. Moeller, J. org. Chem. 26, 1136 (1961)). The first representatives of this class of compound did not become known until 1963 (N. C. Hansen, Acta. chem. scand. 17, 2141 (1963)). With this method, unfortunately, only a few linear alkylaminosulfonyl chlorides, namely ethyl-, n-propyl-, n-butyl- and n-pentylaminosulfonyl chloride, can be prepared in poor yields. Thus Hansen states in the same reference: "When the hydrochlorides of methyl-, hexyl-, cyclohexyl- and octylamine were used, the yelds were too low to permit the isolation of monoalkylsulfamylchlorides". This was later confirmed in German Patent 1,242,627: "Various alkylammonium chlorides, e.g. methylammonium chloride, react with such a poor yield that no N-alkylaminosulfonyl chloride can be isolated". α-linear types are not accessible at all by Hansen's method.

Another serious drawback is the fact that in spite of the lenghy reaction time of at least 18 hours, at most half of the hydrochloride used is reacted. In order to purify the alkylaminosulfonyl chlorides formed merely as byproducts, the remaining hydrochloride had to be precipitated with absolute ether and suction filtered and the filtrate concentrated. To access the technical advance of this process, particularly when operated on an industrial scale, the yields disclosed by Hansen must be referred to the total amount of hydrochloride used and obtained, if the space-time yield is to be determined.

| R | RNH$_2$ . HCl a used | b recd. | SO$_2$Cl$_2$ g | excess % | RNHSO$_2$Cl yield based on a % | yield based on a + b % |
|---|---|---|---|---|---|---|
| C$_2$H$_5$— | 52 | 23 | 341 | 396 | 42 | 29 |
| n-C$_3$H$_7$— | 52 | 26 | 582 | 795 | 13 | 9 |
| n-C$_4$H$_9$— | 77 | 27 | 750 | 790 | 39 | 29 |
| n-C$_5$H$_{11}$— | 19 | 12 | 250 | 1200 | 8 | 5 |

The resulting space-time yield for n-propylaminosulfonyl chloride, for example, is 0.036 kg/l/day. Such low yields of impure raw products do not permit the process to be scaled up to plant practice. The actual yields are even lower because pure compounds are obtained only after repeated distillation.

Although Hansen uses an excess of 1200% of sulfuryl chloride in the case of n-pentylaminosulfonyl chloride for example, he states on page 2142, loc. cit.: "At the end of this period most of the sulfurylchloride had generally disappeared even if a 1 m long Allin n-type condensor was employed. In some cases, therefore, more sulfuryl chloride was adding during the reaction".

These high sulfuryl chloride losses do not allow the process to be operated on a commercial scale on grounds of environmental protection either, because it must be assumed that 4 moles of sodium hydroxide solution are required to neutralize 1 mole of sulfuryl chloride. With an excess of 1200% of sulfuryl chloride more than 4000% of alkali would be needed to destroy the off-gas. The resulting salt load prohibits the discharge of the waste water into rivers.

A further serious disadvantage is the use of absolute ether for separating the hydrochloride. On account of its low flash point and its tendency to form explosive peroxides in the presence of atmospheric oxygen, its use in industrial processes is problematical.

There has been no lack of experiments carried out to overcome the serious drawbacks of the process. For example Schulze and Weiss were successful in improving yields by using acetonitrile as a solvent and metal halides as catalysts (German Patent 1,242,627). In spite of this advance, yields drop considerably in the case of higher alkylaminosulfonyl chlorides. In another publication the inventors define the scope of the process as follows: "The hydrochlorides of aniline and of alkyl amines with longer chain or branched alkyls cannot be reacted; here, too, the chlorinating action of the sulfuryl chloride predominates." (Ann. 729, 43 (1969)).

Another disadvantage is the long reaction times (24 hours) and the large excess of sulfuryl chloride. There is also the problem of the chlorination of acetonitrile in the presence of hydrogen chloride to trichloroacetonitrile which is then trimerized to triperchloromethyltriazine (German Patent 682,391). Some of the triazine distills with the alkylaminosulfonyl chloride, some of it remaining in the distillation residue, with the result that no pure end products are obtained either.

It is an object of this invention to provide a new process for producting in a simpler and more economical manner sulfamic acid halides in better yield and higher purity.

A further object of this invention is the new sulfamic acid halides themselves.

We have found that sulfamic acid halides of the formula $$R-\underset{H}{\underset{|}{N}}-SO_2X \qquad \text{I,}$$

in which R is alkyl of 1 to 20 carbon atoms, cycloalkyl of 4 to 8 carbon atoms or norbornyl, and X is chlorine or bromine with the proviso that said radical R may bear an inert substituent selected from the group consisting of chlorine, bromine, alkyl of 1 to 4 carbon atoms, alkoxycarbonyl of 2 to 4 carbon atoms, cycloalkyl of 4 to 6 carbon atoms and norbornyl, are obtained by reacting a sulfamic acid of the formula $$R-\underset{H}{\underset{|}{N}}-SO_3H \qquad \text{II,}$$

in which R has the above meanings or a metal salt of said acid, with an acid halide of the formula $$Z-X \qquad \text{IV,}$$

in which X is chlorine or bromine and z is the acyl radical of sulfurous acid, phosphoric acid, phosphorous acid, carbonic acid or oxalic acid in a molar ratio of 1 to 2 moles of acid halide per mole of starting material II at a temperature of 10° to 120° C.

We have also found a new sulfamic acid halide of the formula

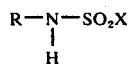

in which R is cyclopentyl, cyclobutyl, cyclooctyl, cycloheptyl, an alkyl radical of 3 to 5 carbon atoms substituted by chlorine atoms or bromine atoms, alkyl of 2 to 5 carbon atoms substituted by cycloalkyl of 4 to 6 carbon atoms or norbornyl; branched alkyl of 5 carbon atoms; 1-methyl-1-propyl; or alkyl of 6 to 20 carbon atoms; and X is chlorine or bromine.

We have also found a new preferred sulfamic acid halide of the formula

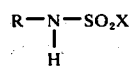

in which R is cyclobutyl, cyclopentyl, sec-butyl, 1-ethylpropyl-1, 3-chloropropyl, 1,2-dimethylbutyl-1, 1-ethyl-2-methylpropyl-1, 1,2-dimethylpropyl, 2-chloropropyl, 1-chloromethyl-propyl, 1,2,2-trimethylpropyl, 1-(2'-norbornyl)-ethyl, 1,2-dimethylhexyl-, 1-cyclohexyl-1-ethyl or 1,3-dimethylbutyl-1; and X is chlorine or bromine.

We have also found a new particularly preferred sulfamic acid halide of the formula

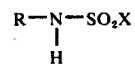

in which R is cyclobutyl, cyclopentyl, sec-butyl, 1-ethylpropyl-1, 3-chloropropyl, 1,2-dimethylbutyl-1, 1-ethyl-2-methylpropyl-1, or 1,3-dimethylbutyl-1 and X is chlorine or bromine.

It has also been found that sulfamic acid halides of the general formula I are obtained in an advantageous manner when a sulfamic acid of the general formula

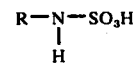 II, in which R has the above meanings, is produced in a first stage from an isocyanate of the general formula

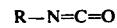 III.

in which R has the above meanings, by reaction with sulfuric acid, and then the product I is produced in a second stage from the product II or its sulfamic acid metal salt by reaction with one of the acid halides mentioned above.

This reaction may be illustrated by the following equation when ethyl sulfamic acid and thionyl chloride are used:

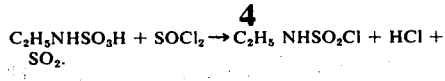

Compared with the known process the process of the invention produces sulfamic acid halides in better yield and with better purity in a simpler and more economical way. The reaction time is shorter and the working up of the reaction mixture, particularly with protection of the environment in mind, is simpler and more dependable. In contrast to the acid halides named, sulfuryl chloride is not suitable as a reactant. Also, starting materials II with alkyl groups of a higher number of carbon atoms can be reacted by the process of the invention. All these advantages results are surprising having regard to the state of the art.

The advantages may be seen from the following comparison with the process described by Hansen.

|  | Comparison | Process of invention |
| --- | --- | --- |
| Excess of halogenating reagent | 400–1200% $SO_2Cl_2$ | 15% $SOCl_2$ |
| Reaction time (hours) | 18 | 2¼–4 |
| Yield | less than 29% | 87% |
| Purification | precipitation with ether 2 distillations | 1 distillation |
| Space-time yield kg/l/day | 0.036 n-propylaminosulfonyl chloride | 1.75 isopropylaminosulfonyl chloride |

The reaction of the invention is surprising because it was not hitherto possible to react sulfamic acids by means of halogenating agents on the sulfonic acid portion. According to the state of the art only a reaction on the basic nitrogen could have been expected in accordance with the reaction of disubstituted amines by means of thionyl chloride:

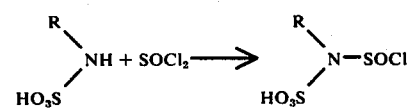

(R. Keat, D. S. Ross and W. Sharp, Spectrochimica Acta, 27, A 1971).

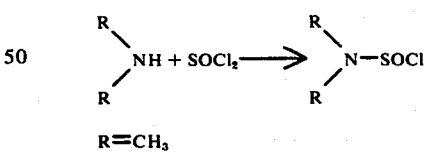

In the case of aromatic sulfonic acids, for example p-hydroxybenzenesulfonic acid, and thionyl chloride, the appropriate sulfonyl chloride can only be prepared with quite specific phosphine catalysts (U.S. Pat. No. 3,673,247, H. W. Hill)

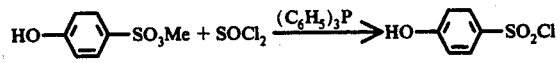

When using Hill's reaction conditions, i.e. triphenyl-phosphine instead of the catalysts of the invention, no alkylaminosulfonyl chlorides are formed.

A. Meuwsen (Gmelins Handbuch der Anorganischen Chemie, 8th edition, Sulfur, Volume 9, Part 3, p. 1592 and 1599) also points out that the sodium salt of mercury amidosulfonic acid reacts with thionyl chloride merely to form the sodium salt of N-sulfinylamidosulfonic acid:

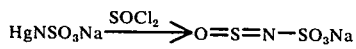

and amidosulfonic acid, which comes closest to the starting materials of the invention, reacts with thionyl chloride to form not sulfamic chloride but the ammonium salt of chlorosulfonic acid

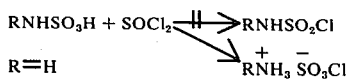

Preferred starting materials II and, accordingly, preferred products I are those in whose formulae R denotes a straight-chain or branched alkyl radical of 1 to 20 particularly 1 to 10, preferably 1 to 8 carbon atoms, a cycloalkyl radical of 4 to 8, preferably 5 to 8, carbon atoms or a norbornyl radical, and X denotes a chlorine or bromine atom. These radicals can be substituted by groups and/or atoms which are inert under the reaction conditions, for example chlorine atoms, bromine atoms, alkyl broups of 1 to 4 carbon atoms, alkoxycarbonyl groups of 2 to 4 carbon atoms, cycloalkyl groups of 4 to 6 carbon atoms and norbornyl groups. Preferred products I are particularly those in whose formula R denotes a cyclopentyl, cycloheptyl, cyclobutyl or cyclooctyl radical; an alkyl radical of 2 to 5, particularly 3 to 5, carbon atoms substituted by chlorine atoms or bromine atoms, an alkyl radical of 2 to 5 carbon atoms substituted by cycloalkyl groups of 4 to 6 carbon atoms or a norbornyl group; a branched alkyl radical of 5 carbon atoms; the 1-methyl-1-propyl radical; or an alkyl radical of 6 to 20, preferably 6 to 10, particularly 6 to 9, carbon atoms and unsubstituted or substituted by chlorine atoms, bromine atoms, alkyl groups of 1 to 4 carbon atoms, alkoxycarbonyl groups of 2 to 4 carbon atoms, cycloalkyl groups of 4 to 6 carbon atoms and norbornyl groups; and X denotes a bromine or chlorine atom.

For example, the following sulfamic acids II are preferred: methylsulfamic acid, ethyl sulfamic acid, n-propylsulfamic acid, isopropylsulfamic acid, n-butylsulfamic acid, isobutylsulfamic acid, sec.-butylsulfamic acid, cyclobutylsulfamic acid, 1-ethyl-propyl-1-sulfamic acid, 1,2-dimethyl-propyl-1-sulfamic acid, n-pentylsulfamic acid, cyclopentylsulfamic acid, n-hexylsulfamic acid, cyclohexylsulfamic acid, cycloheptylsulfamic acid, 1-ethyl-2-methylpropylsulfamic acid, 1,2,2,-trimethyl-1-propylsulfamic acid, 1,2- and 1,3-dimethyl-n-butyl-1-sulfamic acid, 1,2-dimethyl-1-n-hexylsulfamid acid, 1-cyclohexyl-1-ethylsulamic acid, 1-(2'-norbornyl)ethylsulfamic acid, 1-chloromethyl-1-propyl-sulfamic acid, 2-chloropropylsulfamic acid, 3-chloropropylsulfamic acid, 3-bromopropylsulfamic acid, cyclooctylsulfamic acid.

The starting materials II are sulfamic acids which may be prepared in a conventional manner, preferably the sulfuric-acid-free sulfamic acids prepared by the process described in DOS 2,164,197, or metal salts of sulfamic acids. Preferred metal salts are alkali metal and particularly alkaline earth metal salts such as magnesium, calcium, lithium, and preferably potassium and particularly sodium sulfamidates. The starting materials II can be reacted with the acid halide in stoichiometric amounts or with an excess of acid halide, preferably in a ratio of 1 to 2, particularly 1, 1 to 2 or 1 to 1,3, preferably 1,1 to 1,3 moles of acid halide per mole of starting material II. Preferred acid halides are those of the formula $$Z - X \qquad \text{IV,}$$

in which X denotes bromine or preferably a chlorine atom and Z denotes the acyl radical of the acids mentioned above, advantageously thionyl bromide, phosphorus pentabromide, phosphorus tribromide, phosgene, oxalyl chloride or oxalyl bromide or preferably thionyl chloride, phosphorus pentachloride, phosphorus trichloride, phosphorus oxychloride.

The reaction is carried out as a rule at a temperature of 10 to 120° C, particularly 60° to 90° C, with or without superatmospheric pressure, continuously or batchwise. Advantageously there is used as catalyst an N,N-disubstituted carboxylic acid amide or preferably a tertiary amine, desirably in an amount of 0.25 to 1.5 weight % based on the acid chloride. Mixtures of the catalysts mentioned can also be used for the reaction. The amine can also be a diamine, an appropriate salt, for example the hydrochloride of the amine, or a quaternary salt. Preferred catalysts are trimethylamine, triethylamine, pyridine, N-dimethylaniline, N-diethylaniline, N-ethylpiperidine, N-methylpyrrolidine, α-, β- and γ-picoline, N-propylpiperidine, quinoline, isoquinoline, quinazoline, quinoxaline, triamylamine, tri-n-butylamine, n-propyl-diisopropylamine, trifurfurylamine, trihexylamine, N-methylimidazole, N-methylpyrrole, 2,6-and 2,4-lutidine, N-(4-pyridyl)-pyridinium chloride-hydrochloride, triethylene diamine, p-dimethylaminopyridine, N-dimethylcyclohexylamine, pyrimidine, acridine, dimethylformamide, diethylformamide, formic acid N-methylanilide, N,N-dimethylacetamide, N-methylpyrrolidone, and tetramethylurea.

The reaction is suitably carried out using product I from a previous batch as solvent or in an organic solvent which is inert under the reaction conditions. Particularly suitable solvents are chlorinated aiphatic hydrocarbons such as methylene chloride, chloroform, carbon tetrachloride, 1,1- and 1,2-dichloroethane, 1,1,1- and 1,1,2-trichloroethane, n-propyl chloride, n-butyl chloride, sec.-butyl chloride, iso-butyl chloride, 1,4-dibromobutane and 1,10-dibromodecane; chlorinated aromatic hydrocarbons such as chlorobenzene, bromobenzene, iodobenzene, o- and m-dichlorobenzene, o- and m-dibromobenzene, o-, m- and p-chlorotoluene and 1,2,4-trichlorobenzene; nitrohydrocarbons such as nitrobenzene, nitromethane, nitroethane, and o-, m- and p-chloronitrobenzene; nitriles such as benzonitrile and m-chlorobenzonitrile; aliphatic and cycloaliphatic hydrocarbons such as hexane, petroleum ether, cyclohexane, pentane and heptane; or appropriate mixtures. In general the solvent or the product I is used in an amount of 0 to 500 weight %, based on the starting material II.

The reaction can for example be carried out as follows: A mixture of starting material II and acid halide, optionally together with catalyst and/or solvent, is maintained at the reaction temperature for 3 to 8 hours. The acid chloride or the starting material II and the solvent can be placed in the vessel and the other component added. The product I is separated from the reaction mixture in conventional manner. For example by fractional distillation. In many cases only the solvent needs to be removed from the mixture because the product remaining as residue is sufficiently pure, without distillation, for further reaction in numerous syntheses.

In an advantageous embodiment the reaction mixture obtained in the production of the starting materil II is used without isolation as the starting mixture for the process of the invention, optionally after addition of solvent and/or catalyst. Preferably the reaction mixture described in DOS 2,164,197 is used as starting mixture. The mixture is obtained in the reaction of isocyanates with waterfree sulfuric acid at a temperature of at least 25° C in an inert solvent, for example in one of the above-mentioned solvents. The following method is preferred:

A mixture of starting material III and solvent, on the one hand, and sulfuric acid or a mixture of sulfuric acid and solvent, on the other hand, are simultaneously but separately from one another added with vigorous stirring to a vessel containing solvent. The addition suitably lasts for from 10 to 55 minutes and frequently occurs with temperatures of 25° to 50° C, the reaction then proceeding at temperatures of at least 50° C. Advantageously there is chosen as solvent the solvent which is also to be used for the process of the invention. Suitably, the catalyst and optionally a further quantity of solvent are now added and the reaction of the invention carried out in the second stage for 3 to 8 hours. Optionally the reaction temperature is varied within the temperature range mentioned above, e.g. it is raised to 80° to 100° C. The separation of the product I follows in the above-mentioned manner.

The compounds obtainable by the process of the invention are valuable starting materials for the production of plant protection agents, dyes and pharmaceuticals. For example, the o-sulfamidobenzoic acids described in U.S. application Ser. No. 221,021, filed Jan. 26, 1972, can be produced from them by reaction with anthranilic acid or its salts. By cyclizing these materials, for example according to the process described in U.S. Pat. No. 3,822,257, there are obtained the 2,1,3-benzothiadiazine-4-one-2,2-dioxides, whose use as plant protection agents and pharmaceuticals is described in that patent. Belgian Patents 757,886 and 702,887 mention further uses. The outstanding herbicidal properties of this class of compounds, which have been little investigated hitherto, are reflected in U.S. Pat. No. 3,621,017 and in U.S. Pat. applications Ser. Nos. 55,277 (filed July 15, 1970) and 258,711 filed June 1, 1972).

Their use as important intermediates for herbicides is also shown in German Patent 1,542,836; furthermore, by the reaction of alkylaminosulfonyl chlorides with sulfenyl chlorides according to the process of German Patent 1,955,356 intermediates for effective fungicides are obtained.

The 2,1,3-benzothiadiazin-(4)-one-2,2-dioxides obtained with N-alkylaminosulfonyl chlorides are not only known to those skilled in the art as herbicides but also exhibit valuable pharmacological properties. For example U.S. Pat. No. 3,041,336 discloses the 3-oxo1,2,6-thiadiazin-1,1-dioxides find practical application as antiphlogistica, antipyretica and analgetica. Moreover, if the new alkylaminosulfonyl chlorides of the invention are reacted with 2-(m-hydroxyphenyl)-4-methyl-1,2,4-oxadiazolidin-3,5-dione, compounds are obtained which are suitable for the selective control of barnyard grass and wild mustard.

Sulfamic acid halides of the general formula

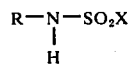

in which R denotes a cyclopentyl, cyclobutyl, cyclopentyl or cyclooctyl radical; an alkyl radical of 2 to 5, particularly 3 to 5, carbon atoms substituted by chlorine atoms or bromine atoms, an alkyl radical of 2 to 5 carbon atoms substituted by cycloalkyl groups of 4 to 6, preferably 5 to 6, carbon atoms or a norbornyl group; a branched alkyl radical of 5 carbon atoms; the 1-methyl-1-propyl radical; or an alkyl radical of 6 to 20, preferably 6 to 10, particularly 6 to 9, carbon atoms which is unsubstituted or substituted in the manner mentioned above; and X denotes a bromine or preferably a chlorine atom; particularly sec.-butylsulfamic acid bromide or preferably chloride, 1-ethylpropyl-1-sulfamic acid bromide or preferably chloride, 1,2-dimethylpropyl-1-sulfamid acid bromide or preferably chloride, 1,2-dimethylbutyl-1-sulfamic acid bromide or preferably chloride, 1,3-dimethylbutyl-1-sulfamic acid bromide or preferably chloride, cyclopentylsulfamic acid bromide or preferably chloride, cyclobutylsulfamic acid bromide or preferably chloride, 2-chloropropylsulfamic acid bromide or preferably chloride, 3-chloropropylsulfamic acid bromide or preferably chloride, 1-chloromethyl-1-propylsulfamic acid bromide or preferably chloride, 1-ethyl-2-methylpropyl-1-sulfamic acid bromide or preferably chloride, 1,2,2-trimethylpropyl-1-sulfamic acid bromide or preferably chloride, 1-(2'-norbornyl)-ethylsulfamic acid bromide or preferably chloride, 1,2-dimethylhexyl-1-sulfamic acid bromide or preferably chloride and 1-cyclohexyl-1-ethylsulfamic acid bromide or preferably chloride; are preferred compounds for the uses mentioned above.

The compound particularly preferred for the uses mentioned above is a sulfamic acid halide of the formula

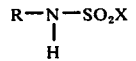

in which R is cyclopentyl, sec-butyl, 1-ethylpropyl-1, 3-chloropropyl, 1,2-dimethylbutyl-1, 1-ethyl-2-methylpropyl-1 or 1,3-dimethylbutyl-1; and x is chlorine or bromine Of these end products I the most advantageous are those in which R is sec.-butyl, cyclopentyl, 1-ethyl-propyl-1, 1,3-dimethylbutyl-1, 3-chloropropyl.

The invention is further illustrated by the following Examples in which the parts are parts by weight.

EXAMPLE 1

To 125 parts of ethylsulfamic acid suspended in 250 parts of carbon tetrachloride are added 0.4 parts of pyridine and 131 parts of thionyl chloride with stirring. The mixture is stirred for five hours at 79° C until the evolution of gas has ended. After the separation of the solvent and excess thionyl chloride the residue is distilled. 125 parts (87% of theory) of ethylamidosulfamic acid chloride boiling at 67° C (0.01 mm) are obtained.

EXAMPLE 2 a. 210 parts of isopropylsulfamic acid are heated under reflux (83° C) in 450 parts of 1,2-dichloroethane and combined with 205 parts of thionyl chloride slowly in the couse of two hours whilst stirring. The mixture is then stirred at 85° to 80° C for 2 hours. After concentration and distillation of the reaction mixture 202 parts (85.3% of theory) of isopropylamidosulfamic acid chloride boiling at 69° C (0.05 mm); $n_D^{25} = 1.4512$ are obtained.

b. 55.7 parts of phosphorus pentachloride are added to 83.3 parts of isopropylsulfamic acid in 310 parts of chloroform. Vigorous evolution of gas occurs as soon as the components are mixed. The mixture is heated for two and a half hours under reflux (83° C) and then distilled. 52 parts (55% of theory) of isopropylsulfamic acid chloride are obtained ($n_D^{25} = 1.4499$; b.p. 69° C at 0.05 mm).

c. 210 parts of isopropylsulfamic acid are reacted without using a solvent with 1.5 parts of pyridine and 220 parts of thionyl chloride for six hours at 70° to 87° C. After distillation of the mixture 178 parts (75% of theory) of isopropylsulfamic acid chloride are obtained.

EXAMPLE 3 a. 16.0 parts of n-propylsulfamic acid in 105 parts of chloroform and 1.46 parts of dimethylformamide are reacted in the course of four hours with 24.6 parts of phosgene at 65° C. After removal of the solvent and distillation of the mixture 8 parts (44.5% of theory) of propylsulfamic acid chloride are obtained (b.p. 73° C at 0.05 mm).

b. 18.5 parts of the sodium salt of propylsulfamic acid in 75 parts of chlorobenzene and 1.13 parts of dimethylformamide are reacted at 85° C in the course of three hours with 28.5 parts of phosgene. 7.1 parts (39.3% of theory) of propylsulfamic acid chloride are obtained (b.p. 74° C at 0.06 mm).

EXAMPLE 4

99.1 parts of n-butyl isocyanate and 100 parts of oleum (2 weight% $SO_3$) are separately added at 25° to 35° C to 280 parts of 1,2-dichloroethane with stirring in the course of 30 minutes. The mixture is stirred for 15 minutes at 84° C. After addition of 0.4 parts of γ-picoline at 84° C 131 parts of thionyl chloride are added in the course of one hour at the same temperature. The mixture is then stirred for three hours at 84° to 87° C. After distillation 126 parts (83.3% of theory) of butylsulfamic acid chloride are obtained (b.p. 88° C at 0.05 mm).

EXAMPLES 5–19

The compounds shown in the Table are produced in accordance with the method of Example 4. The sulfamic acid chlorides of Examples 7–10, 12 and 13 which are not characterizable by distillation were characterized in the form of their o-sulfamoyl-anthranilic acids. The production of the anthranilic acid derivative takes place by reaction of the product I with anthranilic acid at 25° C in chlorobenzene for two hours in accordance with the process described in U.S. application Ser. No. 221,021, filed Jan. 26, 1972.

Table

| Ex | Parts Starting material | RNCO R= | Parts Product I R—NH—SO$_2$Cl | % of theory | Boiling point in ° C/mm | $n_D^{25}$ | | |
|---|---|---|---|---|---|---|---|---|
| 5 | 57 | methyl- | 107 | 83 | 64/0.01 | 1.459 | | m.p. |
| 6 | 89 | sec.-butyl- | 116 | 75 | 89–97/2 | 1.4562 | | 156–157° C |
| 7 | 43.6 | cyclopentyl- | 43.4 | 60 | 120/0.9 | 1.4961 | 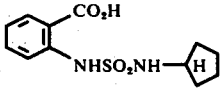 | |
| 8 | 56.6 | 1-ethyl-propyl-1- | 56.5 | 61 | 130/0.3 | 1.4620 | 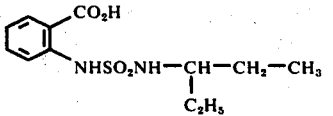 | m.p. 140° C |
| 9 | 57.3 | 1,3-dimethyl-butyl-1- | 62.8 | 70 | — | $n_D^{29}$ = 1.449 | 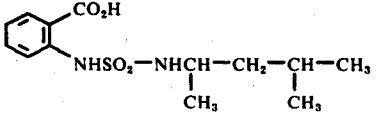 | m.p. 120–122° C |
| 10 | 80 | 1-ethyl-2-methyl-propyl-1- | 79.5 | 63 | — | 1.4557 | 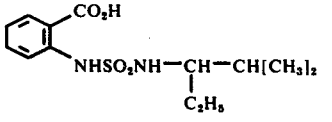 | m.p. 165–167° C |
| 11 | 49.8 | 1-cyclohexyl-ethyl-1- | 55 | 75 | — | 1.4862 | 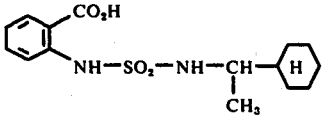 | m.p. 135–141° C |

Table-continued

| Ex | Parts Starting material | RNCO R= | Parts Product I R—NH—SO₂Cl | % of theory | Boiling point in °C/mm | $n_D^{25}$ | | |
|---|---|---|---|---|---|---|---|---|
| 12 | 60.9 | 1,2-dimethyl-hexyl-1- | 44.4 | 50 | 128/0.4 | 1.4639 | 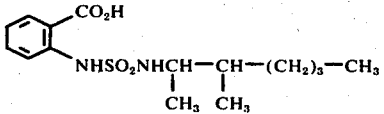 | m.p. 88–93° C |
| 13 | 72.3 | 2-chloro-propyl-1- | 31.4 | 27 | 102–106/3 | 1.4931 | 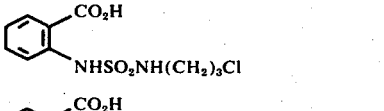 | m.p. 136–137° C |
| 14 | 59.8 | 3-chloro-propyl-1- | 79.7 | 83 | — | 1.487 | | |
| 15 | 110 | 1-chloro-methyl-propyl-1- | 51 | 30 | — | $n_D^{27}$ = 1.481 | 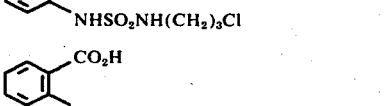 | m.p. 164–167° C |
| 16 | 90 | 1,1-di-methyl-2-chloroethyl-1- | 29 | 21 | 90/2.5 | 1.5030 | | |
| 17 | 101 | 1,2-dimethyl-butyl-1- | 64 | 40 | 108–112/2.5 | 1.4670 | | |
| 18 | 91 | 1-ethyl-pentyl-1- | 44 | 32 | 110/0.2 | 1.4623 | | |
| 19 | 99 | tert.-butyl | 27 | 16 | 90–95/0.6 | — | | |

EXAMPLE 20

82.5 parts of 1,2-dimethylpropyl-1-sulfamic acid are suspended in 150 parts of thionyl chloride and thereafter stirred for seven hours at 79° C. After concentration 91.5 parts of a brown oil with $n_D^{25}$ = 1.4601 are obtained, which according to the IR-spectrum has a purity of 70%. It can be characterized in the form of its 1,2-dimethylpropyl-1-sulfamoyl-anthranilic acid of m.p. 139° C in the manner described above.

There now follows further evidence of utility in the form of valuable herbicides.

EXAMPLE 21

34.3 parts of sec.-butylaminosulfonylchloride and 20.2 parts of triethylamine are introduced in the course of 25 minutes at room temperature through 2 feed lines into a solution of 30 parts of 2-(m-hydroxyphenyl)-4-methyl-1,2,4-oxadiazolidin-3,5-dione in 630 parts of acetonitrile. Stirring is continued for 1 hour at 45° C and the mixture is evaporated in vacuo. The residue is taken up in 400 parts of methylene chloride and suction filtered from the insoluble portion. The organic phase is extracted three times with water, each time with 100 parts, dried over magnesium sulfate and then chromatographed using neutral aluminum oxide. After concentration 29 parts of 2-(3-sec.butylaminosulfonyloxyphenyl)-4-methyl-1,2,4-oxadiazolidin-3,5-dione is obtained as colorless crystals with a melting point of 84°–87° C.

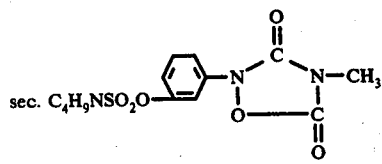

The other compounds are prepared in an analogous manner

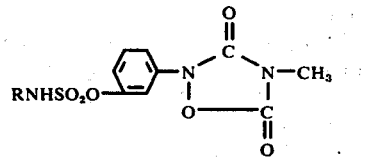

| R | mp (°C) |
|---|---|
| 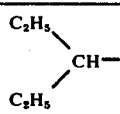 $\begin{matrix}C_2H_5\\C_2H_5\end{matrix}$CH— | $n_D^{25}$ = 1.5288 |
| 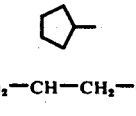 | 99–104 |
| (CH₃)₂—CH—CH₂—CH— <br> $\quad\quad\quad\quad\quad\quad\quad\quad$ CH₃ | 96–99 |
| Cl(CH₂)₃— | 74–78 |

In a greenhouse experimental pots were filled with loamy sandy soil which was then sown with seeds of wheat (*Triticum aestivum*), barley (*Hordeum vulgare*), rye (*Secale cereale*), Indian corn (*Zea mays*), barnyard grass (*Echinochloa crus galli*) and wild mustard (*Sinapis arvensis*). Immediately afterward the soil was treated with 3 kg/ha of each of the following active ingredients
I 2-(3-sec.-butylaminosulfonyloxyphenyl)-4-methyl-1,2,4-oxadiazolidin-3,5-dione
II 2-(3,1'-ethylpropyl-1'-aminosulfonyloxyphenyl)-4-methyl-1,2,4-oxadiazolidin-3,5-dione
III 2-(3-cyclopentylaminosulfonyloxyphenyl)-4-methyl-1,2,4-oxadiazolidin-3,5-dione
IV 2-(3-1',3'-dimethylbutyl-1'-aminosulfonyloxyphenyl)-4-methyl-1,2,4-oxadiazolidin-3,5-dione
V 2-(3-3'-chlorpropylaminosulfonyloxyphenyl)-4-methyl-1,2,4-oxadiazolidin-3,5-dione and in comparison with VI 2-(3-tert.-butylcarbamoyloxyphenyl)-4-methyl-1,2,4-oxadiazolidin3,5-dione each dispersed or emulsified in 500 liters of water per hectare. After 4 to 5 weeks it was observed that compounds I to V exhibited better compatibility with the crop plants and the same herbicidal action as compound VI. The results of the test may be seen from the following Table:

|  | I | II | III | IV | V | VI |
|---|---|---|---|---|---|---|
| Crop plants |  |  |  |  |  |  |
| Triticum aestivum | 0 | 0 | 0 | 0 | 0 | 30 |
| Hordeum vulgare | 0 | 0 | 0 | 0 | 0 | 40 |
| Secale cereale | 0 | 0 | 0 | 0 | 0 | 40 |
| Zea mays | 0 | 0 | 0 | 0 | 0 | 45 |
| Unwanted plants |  |  |  |  |  |  |
| Echinochloa crus galli | 100 | 100 | 100 | 90 | 95 | 100 |
| Sinapis arvensis | 100 | 100 | 90 | 85 | 100 | 100 |

0 = no damage
100 = complete destruction

We claim:

1. A process for the production of a sulfamic acid amide of the formula

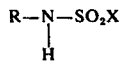         I, in which R is alkyl of 1 to 20 carbon atoms or cycloalkyl of 4 to 8 carbon atoms, and x is chlorine or bromine with the proviso that said radical R may bear an inert substituent selected from the group consisting of chlorine, bromine, alkyl of 1 to 4 carbon atoms, alkoxycarbonyl of 2 to 4 carbon atoms and cycloalkyl of 4 to 6 carbon atoms, which process comprises: reacting a sulfamic acid of the formula

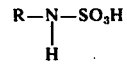         II, in which R has the above meanings or a metal salt of said acid, with an acid halide of the formula

         IV, in which X is chlorine or bromine and Z is the acyl radical of sulfurous acid, phosphoric acid, phosphorous acid, carbonic acid or oxalic acid in a molar ratio of 1 to 2 moles of acide halide per mole of starting material II at a temperature of 10° to 120° C.

2. A process as claimed in claim 1 wherein a sulfamic acid of the formula

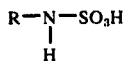         II, in which R has the above meanings, is produced in a first stage from an isocyanate of the general formula

         III, in which R has the above meanings, by reaction with sulfuric acid, and then the product I is produced in a second stage from the product II or a metal salt of that acid by reaction with one of the acid halides specified in claim 1.

3. A process as claimed in claim 1 wherein the reaction is carried out with a magnesium, calcium, lithium, potassium or sodium sulfamidate.

4. A process according to claim 1 wherein the reaction is carried out at a molar ratio of 1.1 to 2 moles of acid halide per mole of starting material II.

5. A process according to claim 1 wherein the reaction is carried out with thionyl chloride, thionyl bromide, phosphorus pentachloride, phosphorus trichloride, phosphorus oxychloride, phosphorus pentabromide, phosphorus tribromide, phosgene oxallyl chloride or oxalyl bromide.

6. A process according to claim 1 wherein the reaction is carried out at a temperature of 60° to 90° C.

7. A process as claimed in claim 1 wherein the reaction is carried out with an N,N-substituted carboxylic acid amid, a tertiary amine, a diamine, an amine salt and/or a quaternary ammonium salt as catalyst.

8. A process as claimed in claim 7 wherein the reaction is carried out with the catalyst in an amount of from 0.25 to 1.5 weight% based on the acid halide.

9. A process as claimed in claim 1 wherein the reaction is carried out in product I as solvent or in an organic solvent which is inert under the reaction conditions.

10. A process as claimed in claim 9 wherein the reaction is carried out with the solvent or product I serving as solvent in an amount of 0 to 500% by weight based on starting material II.

* * * * *